United States Patent [19]

West

[11] 4,373,212
[45] Feb. 15, 1983

[54] LIGHT BLOCKING LENS FOR WELDER HELMET

[75] Inventor: John C. West, Minneapolis, Minn.

[73] Assignee: Century Mfg. Co., Minneapolis, Minn.

[21] Appl. No.: 206,025

[22] Filed: Nov. 12, 1980

[51] Int. Cl.³ .............................................. A61F 9/06
[52] U.S. Cl. ........................................................... 2/8
[58] Field of Search ..................... 2/8, 432, 431, 10

[56] References Cited

U.S. PATENT DOCUMENTS

| | | | |
|---|---|---|---|
| 1,180,341 | 4/1916 | Thomas | 2/432 X |
| 2,002,719 | 5/1935 | Singer | 88/54 |
| 2,152,383 | 3/1939 | Leader | 2/8 |
| 2,748,020 | 5/1956 | Parsons et al. | 117/333 |
| 3,257,667 | 6/1966 | Anderson | 2/8 |
| 3,603,670 | 9/1971 | Kim | 350/260 |
| 4,123,591 | 10/1978 | Karki | 428/454 |
| 4,185,328 | 1/1980 | Graveno | 2/8 |

FOREIGN PATENT DOCUMENTS 686058  1/1940  Fed. Rep. of Germany .............. 2/8

Primary Examiner—Peter P. Nerbun
Attorney, Agent, or Firm—Leo Gregory

[57] ABSTRACT

In the sight opening of the face shield of a welding helmet, a protective lens overlying a filter lens and having a light impervious coating about its edge portion blocking the passage of light rays through its edge portion and through the clearance about the lenses within the sight opening and thus eliminating the use of a gasket or other sealant about the lens first mentioned or within or about the sight opening.

1 Claim, 5 Drawing Figures

LIGHT BLOCKING LENS FOR WELDER HELMET

BACKGROUND OF THE INVENTION

1. Field of the Invention

This invention relates to a lens within the face shield of a welding helmet adapted to prevent the passage of light through the edge portion thereof.

2. Description of the Previous Art

The general practice to prevent the passage of light rays through the edge portion of a lens within the sight opening of the face shield of a welding helmet is to provide a seal such as a gasket to have the lens seated therein or to otherwise seal the lens or sight opening to block the passage of light through the clearance about the lens. The light which passes through the edge portion of the plain protective lens and through the clearance thereabout creates a disturbing halo effect within the face shield.

SUMMARY OF THE INVENTION

The invention herein represents an improvement in means used to block the passage of light through the edge portion of the plain or protective lens within the sight opening of the face shield of a welding helmet.

It is a general practice to place an inexpensive plain glass lens within the sight opening of the face shield of a welding helmet to overlie and protect the relatively expensive filter lens used to protect the eyes of the operator from the glare of a welding arc.

Light rays will pass through the edge portion of the plain glass lens and the through clearance thereabout and thus creates a halo effect within the face shield. The halo effect is disturbing to the operator.

To avoid a halo effect, gaskets are in common use in which to seat the outer protective lens or otherwise seal the lens or sight opening.

It is an object of the invention herein to form the plain glass outer protective lens in such a manner as to prevent the passage of light through the edge portions thereof, thus making unnecessary the use of any separate light sealing means.

It is another object of the invention herein to provide an inexpensive and simple means which does not add and additional or separate structure in blocking the passage of light through the edge portion of the outer protective lens in the face shield of a welding helmet.

More specifically, it is an object of this invention to block the passage of light through the edge portion of the plain glass protective lens which overlies the filter lens within the lens or sight opening of a face shield of a welding helmet by coating the edge portion of said plain glass lens with light impervious coating which effectively blocks the passage of light through said edge portion and prevents a halo effect from occurring within the face shield.

These and other objects and advantages of the invention will be set forth in the following description made in connection with the accompanying drawings in which like reference characters refer to similar parts throughout the several views.

DESCRIPTION OF A PREFERRED EMBODIMENT

Figure 1:
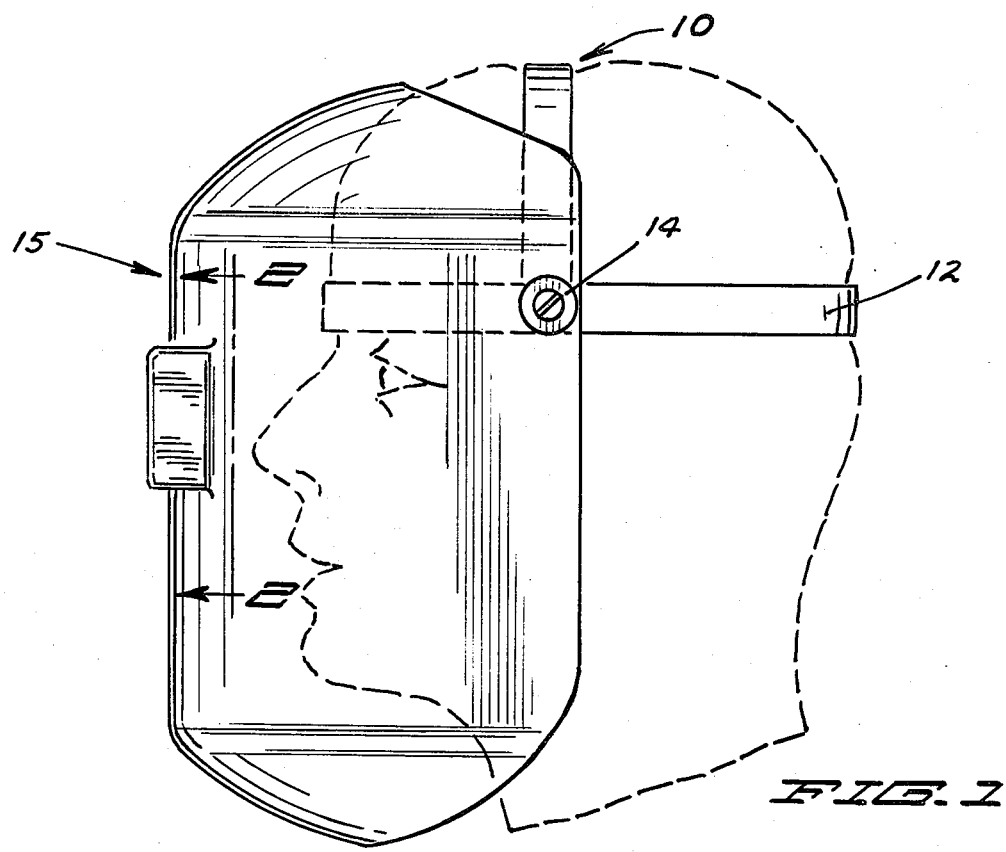
FIG. 1 is a view in side elevation with a portion shown in dotted line for purpose of illustration.
Figure 2:
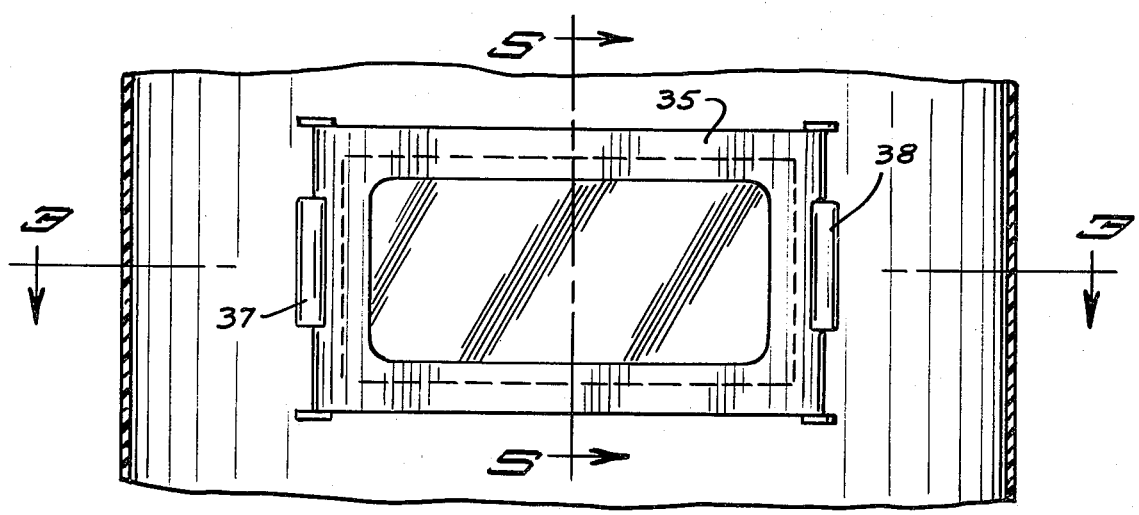
FIG. 2 is a view in vertical section taken on line 2—2 of FIG. 1 as indicated.

Referring to the drawings, a welders helmet is indicated generally by the reference numeral 10, said helmet consisting of a conventional strap head cap portion 12 pivoted to each side thereof, as at 14, is a face shield 15 of a conventional configuration.

The novelty herein is embodied in the treatment of the outer or protective lens member 27 to prevent passage of light rays through the edge portion thereof as will be described.

As is common in the construction of a face shield, a sight opening 18 is formed in the face shield and if the face shield is molded or die cut, the opening will be embodied in the forming of the shield. The sight opening is here shown to be substantially rectangular in plan projecting forwardly of the face shield and forming a wall 20 thereabout. The shield is curved in horizontal section as viewed in FIG. 3 and thus the central wall portion of the sight opening is relatively shallow. Said sight opening has a flange 22 extending inwardly thereabout framing the open front wall 21 thereof. Formed within said sight opening is a chamber 25.

Seated within said sight opening bearing against said flange 22 is said lens 27 which is formed of plain clear glass. Overlying the inward side of said lens is a rectangular frame-like spacer 29 and bearing against the inner side of said spacer is a filter or shaded lens 31. This is a fairly expensive lens which protects the eyes of the operator from the harmful glare of a welding arc.

Securely said lenses within said sight opening is a spring-like retainer 35 which is of a frame-like rectangular form. The ends 35b and 35c of said member 35 are centrally inwardly offset and engage and are held by the projecting ear members 37 and 38 formed in the process of molding the face shield.

Figure 3:
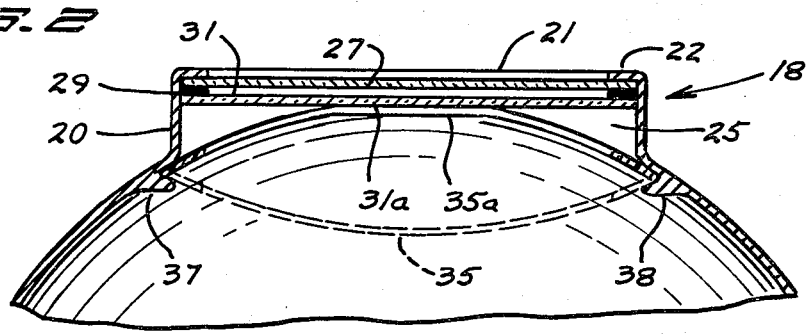
FIG. 3 is a view in horizontal section taken in line 3—3 of FIG. 2 as indicated with a portion thereof shown in dotted line in an alternate position.
Figure 4:
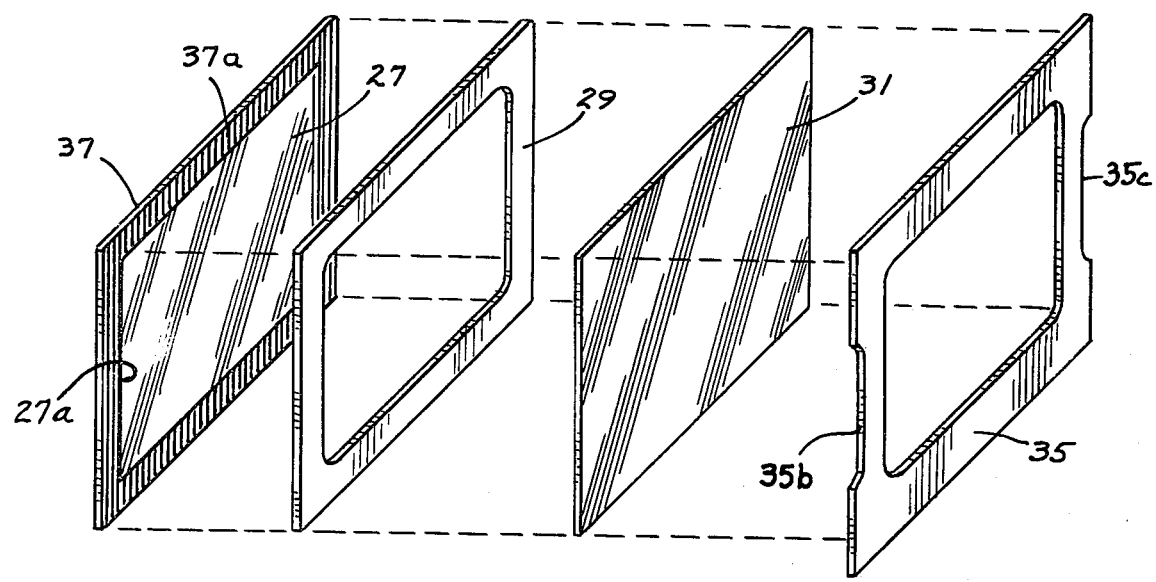
FIG. 4 is an exploded view showing the arrangement of the elements in the sight opening of the face shield.
Figure 5:
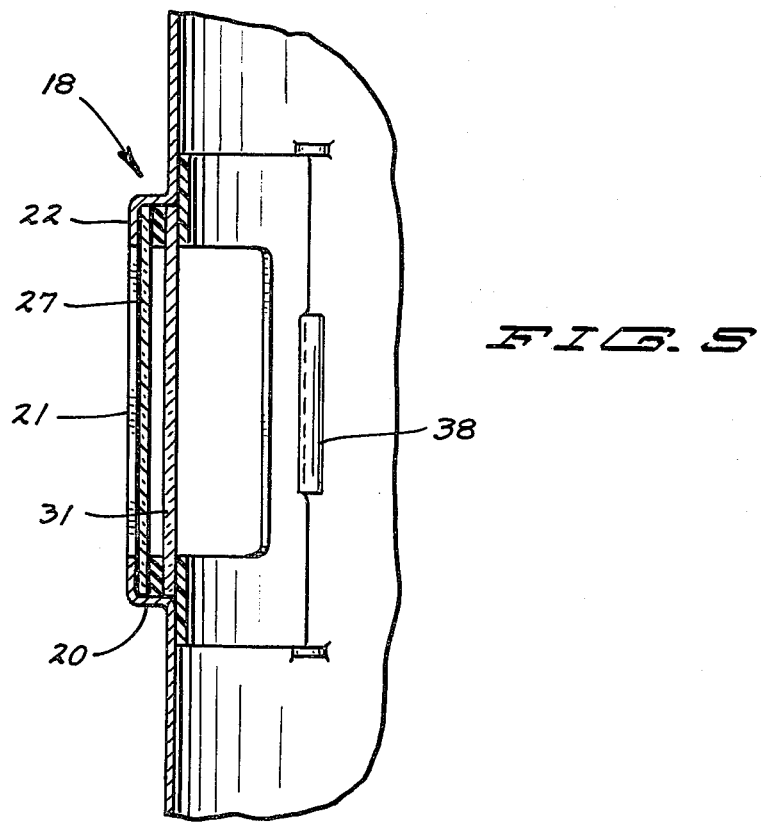
FIG. 5 is a view in vertical section taken on line 5—5 of FIG. 2 as indicated.

With reference to FIG. 3, the retaining member is snapped or sprung into holding position from its dotted 35 position as shown on its full line position 35a bearing against the edge portion of adjacent said filter lens member 31 with its central portion being deflected as a result of its pressure in bearing against said lens.

The essential purpose of the plain lens 27 is to protect the relatively expensive filter lens 31 from damage. However, the plain lens will permit the passage of light rays through the edge portions thereof and through the clearance thereabout within the sight opening and through the clearance about the filter lens to create a disturbing halo effect within the face shield.

Said disturbing halo effect is overcome by light blocking means 37 applied to the edge portion 27a of said lens 27 and which comprises an appropriate coating which is impervious to the passage of light or light rays which would otherwise reflect and pass through the edge portion of said lens 27. Said coating may consist of a liquid such as a paint having sufficient pigment to fully obstruct and prevent the passage of light. Such a paint is a readily available shelf item. Said lens coating 37 may also be applied to frame the sides of said lens as at 37a.

Thus in a very simple and efficient manner the passage of light rays through the edge portion protective lens 27 is prevented and a halo effect is entirely eliminated from the face shield of a welding helmet.

It will of course be understood that various changes may be made in form, details, arrangement and proportions of the parts without departing from the scope of the invention herein which, generally stated, consists in an apparatus capable of carrying out the objects above set forth, in the parts and combinations of parts disclosed and defined in the appended claims.

What is claimed is:

1. A welding helmet arranged and constructed to avoid a halo effect within the face shield thereof, having in combination a face shield of a welding helmet,
a sight opening within said face shield,
a flange extending inwardly of said sight opening forming the perimeter thereof,
a lens disposed within said sight opening having its edge portions bearing against said flange,
said lens having the entire edge portion thereabout caused to be impervious to the passage of light,
a filter lens underlying said first mentioned lens,
a spacer disposed between said first and second mentioned lenses,
inward projections formed at each side edge portion of said sight opening inwardly thereof, and
a spring-like frame member engaging said projections with its respective end portions and being biased outwardly of said filter lens by said projections and being snapped inwardly against said filter lens for positive engagement of said edge portion of said first mentioned lens against said flange.

* * * * *